(12) United States Patent
Stiefel

(10) Patent No.: US 7,022,332 B2
(45) Date of Patent: Apr. 4, 2006

(54) SULFACETAMIDE FORMULATIONS FOR TREATMENT OF ROSACEA

(75) Inventor: Charles W. Stiefel, Miami, FL (US)

(73) Assignee: Stiefel Laboratories, Inc., Oak Hill, NY (US)

( * ) Notice: Subject to any disclaimer, the term of this patent is extended or adjusted under 35 U.S.C. 154(b) by 264 days.

(21) Appl. No.: 10/191,880

(22) Filed: Jul. 9, 2002

(65) Prior Publication Data

US 2003/0118526 A1    Jun. 26, 2003

Related U.S. Application Data

(60) Provisional application No. 60/304,019, filed on Jul. 9, 2001.

(51) Int. Cl.
*A61K 7/00* (2006.01)
*A61K 7/42* (2006.01)
*A61K 7/44* (2006.01)
*A61K 33/04* (2006.01)

(52) U.S. Cl. .......................... 424/401; 424/59; 424/60; 424/400; 424/703; 514/859; 514/861; 514/863; 514/864

(58) Field of Classification Search ................ 424/400, 424/401, 59, 60, 702; 514/859, 861, 863, 514/864
See application file for complete search history.

(56) References Cited

U.S. PATENT DOCUMENTS

| 4,895,727 A | * | 1/1990 | Allen .......................... 424/642 |
| 5,017,366 A | | 5/1991 | Stiefel et al. |
| 6,482,839 B1 | * | 11/2002 | Thornfeldt .................. 514/345 |

OTHER PUBLICATIONS

E. Bonnar, et al., The Demodex mite population in rosacea, Journal of the American Academy of Dermatology, Mar. 1993, pp. 443-448.
Johnathan K. Wilkin, Flushing Disorders, Principles and Practice of Dermatology, Sams and Lynch Editors, 1990, pp. 495-500.
A.P. Kelly, Rosacea, Priciples and Practice of Dermatology, Sams and Lynch Editors, 1990, pp. 789-791.
Food and Drug Administration, Sunscreen Drug Products for Over-The-Counter Human Use, Final Monograph, Federal Register, May 21, 1999, vol. 64, No. 98, pp. 1-54.

* cited by examiner

*Primary Examiner*—Shelly A. Dodson
(74) *Attorney, Agent, or Firm*—Lott & Friedland, P.A.; Michael J. Keller; Ury Fischer

(57) ABSTRACT

The present invention provides improved sulfacetamide and sulfur formulations including sunscreens for the treatment of rosacea.

60 Claims, No Drawings

SULFACETAMIDE FORMULATIONS FOR TREATMENT OF ROSACEA

CLAIM OF PRIORITY

This application is related to provisional application Ser. No. 60/304,019 filed on Jul. 9, 2001 based upon which priority is claimed pursuant to 35 U.S.C. § 119(e) and which is incorporated herein by reference in its entirety.

TECHNICAL FIELD

This invention relates to sulfactemide formulations for the treatment of rosacea.

BACKGROUND OF THE INVENTION

Rosacea is an acne form condition primarily affecting the areas of the nose, cheeks, and forehead of adults. The condition is characterized by erythema, papules, rhinophyma, and telagiectases. The cause of rosacea is unknown, however, dietary influence, gastrointestinal disturbances, psychologic or hormonal imbalance, sebaceous gland abnormalities, and infection have been considered but not validated. Other theories range from solar-induced dermal connective tissue damage, with resultant vascular distension to humorally mediated active vasodilatory changes. A causative role has also been suggested for the hair follicle mite, Demodex, C. E. Bonnard, et al., *The Demodex Mite Population*, J. Amer. Acad. Dermatology, Vol. 28, No. 3, pp. 443–447, March 1993.

Sodium sulfacetamide with and without sulfur has been utilized for many years to treat acne. A nominal treatment concentration for sodium sulfacetamide is 10% and for sulfur is 5%. Sulfacet R® by Dermik Laboratories is a marketed example of such products.

Sulfur alone has been used to treat skin diseases, such as acne, for over 100 years. Sulfur products have been used at levels up to 10% to treat acne. Sulfur has also been combined with resorcinol to improve its performance.

The use of UV absorbers to counteract the sensitizing effects of some dermatological therapeutics has been described in the art. For example, the use of UV absorbers in combination with erythromycin for the treatment of acne is described in U.S. Pat. No. 5,017,366.

A. P. Kelly (Principles and Practice of Dermatology, Sams and Lynch editors, 1990, p. 789) indicates that avoidance of sun exposure is a mechanism to be explored in the management of the skin flushing often seen with rosacea. J. K. Wilkins stated (Id, p. 495) that "the degree to which reddening occurs results not only from the intensity of the flushing reaction, but also from the pigmentation of the subject and the visibility of the vessels, which may be enhanced in a sun-damaged dystrophic dermis."

Many skin disorders are treated with a single course of therapy on the premise that the etiology and presented symptoms are the result of a single cause. Unfortunately, many diseases, especially skin diseases, are complicated in that the symptoms may be the result of changes in internal, external, or a combination of both environments. As a result, conventional single agent therapies have been shown not to yield the desired clinical results demonstrated, for example, as cosmetic improvement (appearance), elimination of pathogenic organisms, reduction of swelling, etc. Skin disorders where two or more conditions have been identified include acne and rosacea.

Antibacterial compositions for dermatological treatment must remain stable for long periods of time (useful shelf life), not lose its potency (a known characteristic of antibiotics under certain conditions), not form insoluble substances or complexes because of the combining sulfacetamide and other active ingredients, and also not be especially irritating to the skin.

Sunscreens are designed to protect against sunburn caused by UVB rays and generally provide little protection against UVA rays. UVA rays are linked to aging and generally have a depressing effect on the immune system and therefore may lead to other dermatological problems such as rosacea.

Missing in the art is a convenient means to ensure patient compliance with topical administration of a sulfacetamide and a sunscreen. At present, there is no commercially available product containing both a sulfacetamide and a sunscreen.

SUMMARY OF THE INVENTION

The present invention is directed towards a topical composition for the treatment of mammalian skin dermatoses comprising a sulfacetamide or a derivative thereof and at least 1 sunscreen. This invention is also directed toward a method of treating mammalian dermatoses by administering a topical composition comprising a sulfacetamide or a derivative thereof and at least 1 sunscreen. This invention is also directed towards a topical composition for the treatment of mammalian skin dermatoses comprising sulfacetamide and at least one sunscreen, wherein the composition is chemically stable for more than 180 days at 25° C. This invention is also directed towards a topical composition for the treatment of mammalian skin dermatoses comprising sulfacetamide and at least one sunscreen, wherein the composition exhibits less than 10% decomposition of sulfacetamide or sunscreen after storage at 25° C. for 180 days.

DETAILED DESCRIPTION OF THE INVENTION

The present invention comprises a sulfacetamide and a sunscreen in combination for the treatment of rosacea. This combination product is directed to the multifaceted etiology of rosacea. The novel combination of sodium sulfacetamide and a sunscreen described herein offers the clinician a regimen which would be an effective treatment of this often unsightly skin condition.

The topical drug delivery system used to formulate the present invention may be either aqueous, hydro-alcoholic, or non-aqueous in composition and may include polymers, liposomes, surfactants, thickeners, or other pharmaceutically acceptable ingredients which would enhance the product's acceptance. Such formulations are generally known in the art.

A preferred topical delivery system is emulsion based. However, other topical pharmaceutical dosage forms, such as suspensions, should also be operative. The active ingredients may be dissolved, dispersed, suspended, solubilized, coated, entrapped, or encapsulated within the formulation matrix by a variety of techniques known in the art.

Acceptable levels of sodium sulfacetamide are from 1 to 20%, more preferably 5 to 15%. Acceptable levels of sulfur are from 1 to 20%, more preferably from 2.5 to 10%. While the preferred sulfacetamide is sodium sulfacetamide, other salts and derivatives which function in the treatment of mammalian skin dermatoses would also be suitable.

A variety of UV absorbers are known in the art and have varying effectiveness at absorbing different parts of the UV spectrum. A preferred embodiment of the present invention would include a UV absorber component that has activity in both the UVA and UVB ranges. This may be accomplished either through the use of a UV absorber that is effective in both the UVA and the UVB ranges or through the use of two or more UV absorbers having combined activity across the UVA and UVB spectra.

UV absorbers encompassed by this invention include, but are not limited to, the use of one or more of the following: benzophenone derivatives (such as benzophenone-1, benzophenone-2 or benzophenone-3 [also known as oxybenzone], benzophenone-4, benzophenone-6, benzophenone-8, benzophenone-12, alkyl and aryl cinnamate derivatives (such as DEA methoxycinnamate, octyl methoxycinnamate), aminobenzoate derivatives (such as p-aminobenzoic acid, ethyl dihydroxypropyl p-amino benzoic acid glyceryl p-aminobenzoic acid, octyl dimethyl p-aminobenzoic acid), homosalate, anthranilate derivatives (such as menthyl anthranilate), aryl acrylate derivatives (such as etocrylene, octocrylene), salicylate derivatives (such as octyl salicylate, trolamine salicylate), benzimidazole derivatives (such as 2-phenylbenzimidazole-5 sulphonic acid), benzilidene derivatives (such as 3-(4-methylbenzylidene)-camphor), benzoyl methane derivatives ( such as 4-isopropyl dibenzoyl methane, butyl methoxy dibenzoyl methane [also known as avobenzone]) and oxides (such as titanium dioxide and zinc oxide).

The amount of UV absorber employed will depend on its effectiveness, alone or in combination with other UV absorbers, but in any event will be sufficient to block a measurable quantity of UV radiation, preferably that UV radiation generated naturally, such as by the sun, or generated by man-made UV radiation generating sources, such as electric lamps and beams.

The most preferred UV absorbers and their concentration by weight is set forth in Table 1.:

TABLE 1

| UV Absorbers & Concentration | |
| --- | --- |
| UV Absorbers | % w/w |
| avobenzone | 0.1 to 5% |
| octocrylene | 0.1 to 15% |
| octyl methoxycinnamate | 0.1 to 10% |
| oxybenzone | 0.1 to 10% |

Compositions embodying the present invention are described in detail the examples that follow. Examples One and Two are most preferred.

EXAMPLE ONE

Ingredients

The ingredients of Example One are set forth in Table 2.

TABLE 2

| Example One Ingredients (% W/W) | |
| --- | --- |
| | % W/W |
| Phase A Ingredients | |
| Purified Water | 49.29 |
| Edetate Disodium | 0.500 |
| Sodium Phosphate Monobasic (Dihydrate) | 0.0100 |

TABLE 2-continued

| Example One Ingredients (% W/W) | |
| --- | --- |
| | % W/W |
| Phase B Ingredients | |
| Cetostearyl Alcohol | 1.50 |
| Steareth-2 | 2.25 |
| Steareth-21 | 2.75 |
| Emulsifying Wax, NF | 4.00 |
| Octyl Methoxycinnamate | 7.50 |
| $C_{12-15}$ Alkyl Benzoate | 5.00 |
| Propylene Glycol | 5.50 |
| Avobenzone | 3.00 |
| Dimethicone | 0.500 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), octyl methoxycinnamate, $C_{12-15}$ alkyl benzoate, propylene glycol, avobenzone and dimethicone. Heat to about 70° C. while mixing to make uniform. To Phase "B" add and disperse the sulfur and sodium sulfacetamide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

Stability Testing

The composition of Example One was placed on stability at FT (Freeze-Thaw; a stability test where the composition is subject to alternating periods of freezing and warm environments), 6° C., 25° C., 30° C., and 40° C. All samples placed on stability were maintained at the constant temperature indicated. The freeze thaw samples were subjected to alternate periods of freezing (−10 to −20° C.) and warmer environments, such as room temperature (15–30° C.). This test is used to accelerate emulsion and solution instability in hopes of finding problems early in development. Each sample was observed weekly for the first 4 weeks and once a month for months two through six. Chemical analysis were completed on samples taken after storage at the designated temperatures for the stated number of days over a six month test period. The results of the chemical analysis are set forth in Table 3 below and the physical observations are set forth in Table 4 below.

TABLE 3

Example One Chemical Analysis

| Ingredient | # Days | Specification (% W/W) | FT | 6° C. | 25° C. | 30° C. | 40° C. |
|---|---|---|---|---|---|---|---|
| Sodium Sulfacetamide | 7 | 9–11 | | | 10.84 | | |
| Sodium Sulfacetamide | 96 | 9–11 | 10.68 | 10.87 | 10.54 | 10.40 | 10.36 |
| Sodium Sulfacetamide | 186 | 9–11 | | 10.94 | 10.70 | 10.61 | 10.06 |
| Sulfur | 7 | 4.5–5.0 | | | 4.75 | | |
| Sulfur | 96 | 4.5–5.0 | 4.88 | 4.79 | 5.10 | 4.91 | 5.04 |
| Sulfur | 186 | 4.5–5.0 | | 4.63 | 4.65 | 4.85 | 5.04 |
| Avobenzone | 7 | 2.7–3.30 | | | 3.00 | | |
| Avobenzone | 96 | 2.7–3.30 | 2.98 | 2.97 | 2.95 | 2.93 | 2.93 |
| Avobenzone | 186 | 2.7–3.30 | | 2.92 | 2.92 | 2.93 | 2.88 |
| Octyl Methoxy cinnamate | 7 | 6.75–8.25 | | | 6.89 | | |
| Octyl Methoxy cinnamate | 96 | 6.75–8.25 | 7.48 | 7.42 | 7.29 | 7.39 | 7.56 |
| Octyl Methoxy cinnamate | 186 | 6.75–8.25 | | 7.48 | 7.44 | 7.44 | 7.50 |
| Benzyl Alcohol | 96 | 0.90–1.10 | 1.12 | 0.99 | 1.01 | 1.01 | 0.97 |
| Benzyl Alcohol | 186 | 0.90–1.10 | | 0.99 | 1.00 | 1.01 | 0.98 |
| pH | 96 | NA | 7.42 | 7.39 | 7.39 | 7.43 | 7.42 |
| pH | 186 | NA | | NA | 7.22 | NA | 7.25 |

TABLE 4

Example One Physical Appearance

| Day | Temperature | Appearance |
|---|---|---|
| 0 | 25° | A pale yellow smooth homogenous cream |
| 7 | All | Same as initial |
| 14 | All | Same as initial |
| 21 | All | Same as initial |
| 28 | All | Same as initial |
| 53 | 40° | Same as initial with slight aeration |
| 53 | All others | Same as initial |
| 95 | FT, 6°, 25° | Same as initial. |
| 95 | 30° | Same as initial with slight aeration |
| 95 | 40° | Product has darkened and become aerated. |
| 186 | All | Same as day 95 |

EXAMPLE TWO

Ingredients

The ingredients of Example 2 are set forth in Table 5.

TABLE 5

Example Two Ingredients (% W/W)

| | % W/W |
|---|---|
| Phase A Ingredients | |
| Purified Water | 43.79 |
| Edetate Disodium | 0.500 |
| Sodium Phosphate Monobasic (Dihydrate) | 0.0100 |
| Phase B Ingredients | |
| Cetostearyl Alcohol | 1.50 |
| Steareth-2 | 2.25 |
| Steareth-21 | 2.75 |
| Emulsifying Wax, NF | 4.00 |
| Oxybenzone | 6.00 |
| $C_{12-15}$ Alkyl Benzoate | 5.00 |
| Propylene Glycol | 5.50 |
| Octocrylene | 10.0 |
| Dimethicone | 0.500 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), oxybenone, $C_{12-15}$ alkyl benzoate, propylene glycol, octocrylene and dimethicone. Heat to about 70° C. while mixing to make uniform. To Phase "B" add and disperse the sulfur and sodium sulfacetamide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

The formulation of Example Two was stored in clear vials capped with black polyseal lined screw caps and tested for stability at 40, 30, 25, 6 and FT. The samples were observed and assayed at 7 days and 3 months.

Stability Testing

The composition of Example Two was placed on stability at FT, 6° C., 25° C., 30° C., and 40° C. Each sample was observed weekly for the first 4 weeks and once a month for months two through six. Chemical analysis were completed on samples taken after storage at the designated temperatures for the stated number of days over a six month test period. The results of the chemical analysis are set forth in Table 6 below and the physical observations are set forth in Table 7 below.

TABLE 6

Example Two Chemical Analysis

| Ingredient | # Days | Specification (% W/W) | FT | 6° C. | 25° C. | 30° C. | 40° C. |
|---|---|---|---|---|---|---|---|
| Sodium Sulfacetamide | 7 | 9–11 | | | 10.60 | | |
| Sodium Sulfacetamide | 96 | 9–11 | 10.67 | 10.61 | 10.68 | 10.34 | 10.19 |
| Sulfur | 7 | 4.5–5.0 | | | 4.63 | | |
| Sulfur | 96 | 4.5–5.0 | 4.97 | 4.92 | 5.12 | 5.45 | 5.36 |
| Octocrylene | 7 | 9.00–11.00 | | | 9.54 | | |
| Octocrylene | 96 | 9.00–11.00 | 9.60 | 9.61 | 9.64 | 8.89 | 9.37 |
| Oxybenzone | 7 | 5.4–6.6 | | | 5.86 | | |
| Oxybenzone | 96 | 5.4–6.6 | 5.99 | 5.97 | 5.99 | 5.51 | 5.84 |
| Benzyl Alcohol | 96 | 0.9–1.10 | .90 | .92 | .90 | .90 | .88 |
| PH | 96 | NA | 7.35 | 7.43 | 7.46 | 7.53 | 7.55 |

TABLE 7

Example Two Physical Appearance

| Day | Temperature | Appearance |
|---|---|---|
| 0 | 25° | A pale yellow smooth homogenous cream |
| 7 | 40° | Slight darkening of product, but otherwise as initial |
| 7 | All others | Same as initial |
| 14 | All | Same as day 7 |
| 21 | 30° | Slightly darker than day 7. |
| 21 | 40° | Same as day 7. |
| 21 | All others | Same as initial |
| 28 | All | Same as day 21 |
| 53 | 40° | Same as day 21 with slight aeration |
| 53 | All others | Same as day 28 |
| 95 | FT, 6°, 25° | As initial with very slight aeration |
| 95 | 30° | Product has darkened and become aerated |
| 95 | 40° | Product has become aerated. A brown layer has formed on the bottom ⅓ of the vial with the remaining product being slightly green in color. |
| 186 | 25° | Aeration more pronounced than at 95 days |
| 186 | All others | Same as day 95 |

EXAMPLE THREE

Ingredients

The ingredients of Example Three are set forth in Table 8

TABLE 8

Example Three Ingredients (% W/W)

| | % W/W |
|---|---|
| Phase A Ingredients | |
| Purified Water | 46.29 |
| Edetate Disodium | 0.500 |
| Sodium Phosphate Monobasic (Dihydrate) | 0.0100 |
| Phase B Ingredients | |
| Cetostearyl Alcohol | 2.00 |
| Steareth-2 | 2.00 |
| Steareth-21 | 3.00 |
| Emulsifying Wax, NF | 5.00 |
| Avobenzone | 1.00 |
| C$_{12-15}$ Alkyl Benzoate | 5.00 |
| Propylene Glycol | 4.00 |
| Octyl Methoxycinnamate | 5.00 |
| Dimethicone | 0.500 |
| Zinc Oxide Dispersion | 3.50 |
| Titanium Dioxide Dispersion | 4.00 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), C$_{12-15}$ alkyl benzoate, propylene glycol, and dimethicone. Heat to about 70° C. while mixing to make uniform. To Phase "B" add and disperse the sulfur, sodium sulfacetamide, zinc oxide and titanium dioxide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

Compositions as disclosed herein may be administered to a patient suffering from rosacea by thinly applying the composition topically to affected areas of the face 1–3 times per day.

SPF Testing (In Vitro)

Ten (10) compositions with varying sunscreen components were tested to determine their relative sunscreen protection factor using an in vitro procedure employing the Optometrics Corporation SPF290 instrument. The ten formulations were made according to the procedures set out in Examples One, Two and Three with the only variable being the sunscreen components. Data were generated using Transpore® surgical tape as a substrate. Test materials are applied to the tape and the UV light absorbance measured. Results generated are reported in Table 9. These measurements provide an assessment of potential product SPF the true value of which may only be established in a human clinical evaluation.

TABLE 9

SPF (In Vitro) Testing Results

| Formulation Components | SPF Value | +/− SD |
|---|---|---|
| Sodium Sulfacetamide 10%<br>Sulfur 5%<br>Avobenzone 3%<br>Octyl Methoxycinnamate 7.5%<br>Oxybenzone 6% | 14.9 | 3.0 |
| Sodium Sulfacetamide 10%<br>Sulfur 5%<br>Avobenzone 3%<br>Octocrylene 10%<br>Octyl Methoxycinnamate 7.5% | 12.1 | 2.6 |
| Sulfacetamide Sodium 10%<br>Sulfur 5%<br>Octocrylene 10%<br>Octyl Methoxycinnamate 7.5%<br>Oxybenzone 6% | 11.9 | 2.0 |
| Sodium Sulfacetamide 10%<br>Sulfur 5%<br>Octyl Methoxycinnamate 7.5%<br>Octocrylene 10%<br>Octyl Salicylate 5.0% | 8.3 | 1.2 |
| Sodium Sulfacetamide 10%<br>Sulfur 5%<br>Octyl Methoxycinnamate 7.5%<br>Sulisobenzone 10% | 10.4 | 2.3 |
| Sodium Sulfacetamide 10%<br>Sulfur 5%<br>Octocrylene 10%<br>Octyl Methoxycinnamate 7.5% | 8.3 | 0.7 |
| Sodium Sulfacetamide 10%<br>Sulfur 5%<br>Avobenzone 3%<br>Octyl Methoxycinnamate 7.5% | 11.4 | 3.7 |
| Sodium Sulfacetamide 10%<br>Sulfur 5% | 1.6 | 0.1 |
| Sodium Sulfacetamide 10%<br>Sulfur 5%<br>Octocrylene 10%<br>Oxybenzone 6% | 12.2 | 2.9 |
| Sodium Sulfacetamide 10%<br>Sulfur 5%<br>Avobenzone 3%<br>Octyl Methoxycinnamate 7.5% | 11.6 | 2.2 |

Conclusion

Data generated show that the addition of sunscreen agents increases the relative SPF values found when compared to the product without added sunscreens.

SPF Testing (In Vivo)

Five of the above compositions were tested with a homosalate control to determine their relative sunscreen protection factor by following an FDA approved human clinical study design. Forty-six subjects (43 female, 3 male) with one of the following skin types and sunburn and tanning histories: I) Always burns easily; never tans (sensitive), II) aways burns easily; tans minimally (sensitive), III) burns moderately; tans gradually (normal). Each subject's inherent MED (minimal erythema dose) was determined by exposing the unprotected skin on their backs to ultraviolet radiation in a series of doses or timed intervals. Twenty-two to twenty four hours post exposure the series of doses were evaluated to determine the smallest dose of energy that produced redness reaching the borders of the exposure site (MED). This procedure was repeated concurrently with the test products for confirmation (MED Unprotected Control Site).

The subjects were sequentially placed into two groups. Group 1 tested the first two test articles (as listed in Table 10) and the 8% homosalate control and group 2 tested the second three test articles (as listed in Table 10) and the 8% homosalate control (applied to their backs) with the sequence of test articles predetermined by randomization. A series of seven ultraviolet radiation exposures were administered within each treatment area as outlined in the FDA Final Monograph.

Following exposure of the sub sites with ultraviolet radiation, a visual evaluation was conducted for the presence or absence of an immediate response (darkening, reddening or heat response) and noted. The sub sites were covered and evaluated 22–24 hours after exposure, in a blinded manner, to determine the MED. Reactions to the ultraviolet exposures were graded using a scale of 0–3+ where 0=no reaction, ±=minimal erythema, the first perceptible, redness reaction with clearly defined borders, 1+=defined erythema, 2+=moderate erythema, and 3+=severe erythema. Results generated are reported in Table 10.

Calculation of SPF

For each subject, the SPF value for each test article sunscreen was calculated by dividing the dose of ultraviolet radiation (Joules/cm$^2$ required to produce the MED of the protected skin (MED Protected Skin) by the dose of ultraviolet radiation (joules/cm$^2$ required to produce the MED of the unprotected skin (MED Unprotected Control Site).

The label SPF value for each test article formulation was determined as follows: Calculate the mean SPF value (x). Determine the standard deviation (s). Obtain the upper 5% point from the t distribution table with n−1 degrees of freedom (t). Compute ts/ $\sqrt{n}$ and denote by (A). The label SPF equals the largest whole number less than x−A. (See the FDA Final Monograph: FR May 21, 1999, Vol. 64, No. 98). It is recommended that the standard error be determined and not exceed five percent of the mean.

TABLE 10

SPF (In Vivo) Testing Results

| Formulation Description | SPF Value | ± SD | Label SPF |
|---|---|---|---|
| Sodium Sulfacetamide 10%<br>Sulfur 5%<br>Avobenzone 3%<br>Oxybenzone 6%<br>Octyl Methoxycinnamate 7.5% | 20.6 | 2.6 | 19 |
| Sodium Sulfacetamide 10%<br>Sulfur 5%<br>Avobenzone 3%<br>Octocrylene 10%<br>Octyl Methoxycinnamate 7.5% | 19.9 | 1.8 | 19 |
| Sodium Sulfacetamide 10%<br>Sulfur 5%<br>Octocrylene 10%<br>Octyl Methoxycinnamate 7.5%<br>Oxybenzone 6% | 20.4 | 3.4 | 18 |
| Sodium Sulfacetamide 10%<br>Sulfur 5%<br>Octocrylene 10%<br>Octyl Methoxycinnamate 7.5% | 20.1 | 3.2 | 18 |
| Sodium Sulfacetamide 10%<br>Sulfur 5%<br>Avobenzone 3%<br>Octyl Methoxycinnamate 7.5% | 20.3 | 3.4 | 18 |

Data generated show each of the compositions exhibit a sun protection factor.

What is claimed is:

1. A topical composition for the treatment of mammalian skin dermatoses comprising at least one sulfacetamide or a derivative thereof and at least one sunscreen.

2. The topical composition of claim 1 wherein the sulfacetamide is sodium sulfacetamide.

3. The topical composition of claim 1 used for the treatment of rosacea.

4. The topical composition of claim 1 wherein the formulation further comprises sulfur.

5. The topical composition of claim 1 wherein the sunscreen blocks the absorption of UV radiation.

6. The topical composition of claim 1 wherein the sunscreen absorbs UV A and UV B radiation.

7. The topical composition of claim 6 where the absorption of UV A and UV B is provided by at least two different sunscreens.

8. The topical composition of claim 6 wherein the sunscreen is selected from at least one of the following: avobenzone, octocrylene, octyl methoxycinnamate or oxybenzone.

9. A topical composition of claim 5 wherein the sunscreen is an inorganic oxide.

10. A topical composition of claim 9 wherein the sunscreen is selected from the group of titanium dioxide or zinc oxide.

11. The topical composition of claim 8 wherein the sunscreen is present from about 0.1% to about 25% by weight.

12. The composition of claim 1 wherein the sunscreen is present in a sufficient amount to produce a sun protection factor of at least 2.

13. The topical composition of claim 1 wherein the composition further comprises benzyl alcohol.

14. The topical composition of claim 13 wherein the benzyl alcohol is present from about 0.1 to about 10% by weight.

15. The topical composition of claim 13 wherein the benzyl alcohol is present from about 0.5 to 2.5% by weight.

16. A method of treating mammalian dermatoses by administering a topical composition comprising at least one sulfacetamide or a derivative thereof and at least one sunscreen.

17. The method of 16 wherein the sulfacetamide is sodium sulfacetamide.

18. The method of claim 16 wherein the topical composition further comprises sulfur.

19. The method of claim 16 wherein the sunscreen blocks the absorption of UV radiation.

20. The method of claim 16 wherein sunscreen absorbs UVA and UVB radiation.

21. The method of claim 16 wherein at least two different sunscreens are used to absorb UV A and UVB radiation.

22. The method of claim 16 wherein the sunscreen is selected from at least one of the following: avobenzone, octocrylene, octyl methoxycinnamate or oxybenzone.

23. The method of claim 16 wherein the sunscreen is selected from an inorganic oxide.

24. The method of claim 23 wherein the sunscreen is selected the group consisting of titanium dioxide or zinc oxide.

25. The method of claim 22 wherein the sunscreen is present from about 0.1 to about 10 percent by weight.

26. The method of claim 16 wherein the sunscreen is present in an amount sufficient to produce a sun protection factor of at least 2.

27. The method of claim 16 wherein the sunscreen is present from about 0.1 to about 10 percent by weight.

28. The method of claim 16 wherein topical composition further comprises benzyl alcohol.

29. The method of claim 16 wherein the treatment results in a reduction of redness, inflammation, lesions or microorganisms.

30. The method of claim 16 wherein the wherein the dermatoses is acne, rosacea, or a skin infection.

31. The method of claim 18 wherein treatment results in a reduction of redness, inflammation, lesions or microorganisms.

32. The method of claim 18 wherein the dermatoses is acne, rosacea, or a skin infection.

33. The method of claim 19 wherein treatment results in a reduction of redness, inflammation, lesions or microorganisms.

34. The method of claim 19 wherein the dermatoses is acne, rosacea, or a skin infection.

35. The method of claim 20 where treatment results in a reduction of redness, inflammation, lesions or microorganisms.

36. The method of claim 20 wherein the dermatoses is acne, rosacea, or a skin infection.

37. The method of claim 21 where treatment results in a reduction of redness, inflammation, lesions or microorganisms.

38. The method of claim 21 wherein the dermatoses is acne, rosacea, or a skin infection.

39. The method of claim 22 where treatment results in a reduction of redness, inflammation, lesions or microorganisms.

40. The method of claim 22 wherein the dermatoses is acne, rosacea, or a skin infection.

41. The method of claim 23 where treatment results in a reduction of redness, inflammation, lesions or microorganisms.

42. The method of claim 23 wherein the dermatoses is acne, rosacea, or a skin infection.

43. The method of claim 24 where treatment results in a reduction of redness, inflammation, lesions or microorganisms.

44. The method of claim 24 wherein the dermatoses is acne, rosacea, or a skin infection.

45. The method of claim 25 where treatment results in a reduction of redness, inflammation, lesions or microorganisms.

46. The method of claim 25 wherein the dermatoses is acne, rosacea, or a skin infection.

47. The method of claim 26 where treatment results in a reduction of redness, inflammation, lesions or microorganisms.

48. The method of claim 26 wherein the dermatoses is acne, rosacea, or a skin infection.

49. The method of claim 27 where treatment results in a reduction of redness, inflammation, lesions or microorganisms.

50. The method of claim 27 wherein the dermatoses is acne, rosacea, or a skin infection.

51. A topical composition for the treatment of mammalian skin dermatoses comprising at least one sulfacetamide and at least one sunscreen, wherein the composition is chemically stable for more than 180 days at 25° C.

52. A topical composition for the treatment of mammalian skin dermatoses comprising sulfacetamide and at least one sunscreen, wherein the composition exhibits less than 10% decomposition of claim sulfacetamide or sunscreen after storage at 25° C. for 180 days.

53. The composition of claim 51 wherein the composition further comprises sulfur.

54. The composition of claim 51 wherein the composition further comprises benzyl alcohol.

55. The composition of claim 52 wherein the composition further comprises sulfur.

56. The composition of claim 52 wherein the composition further comprises benzyl alcohol.

57. The composition of claim 51 wherein the sunscreen is selected from at least one of the following: avobenzone, octocrylene, octyl methoxycinnamate, oxybenzone, zinc oxide or titanium oxide.

58. The composition of claim 52 wherein the sunscreen is selected from at least one of the following: avobenzone, octocrylene, octyl methoxycinnamate, oxybenzone, zinc oxide or titanium oxide.

59. The composition of claim 51 wherein the sunscreen is present in an amount sufficient to provide a sun protection factor of at least 2.

60. The composition of claim 52 wherein the sunscreen is present in an amount sufficient to provide a sun protection factor of at least 2.

* * * * *

US007022332C1

(12) INTER PARTES REEXAMINATION CERTIFICATE (0043rd)

United States Patent
Stiefel

(10) Number: US 7,022,332 C1
(45) Certificate Issued: Dec. 2, 2008

(54) SULFACETAMIDE FORMULATIONS FOR TREATMENT OF ROSACEA

(75) Inventor: Charles W. Stiefel, Miami, FL (US)

(73) Assignee: Stiefel Laboratories, Inc., Oak Hill, NY (US)

Reexamination Request:
No. 95/000,143, Apr. 13, 2006

Reexamination Certificate for:
Patent No.: 7,022,332
Issued: Apr. 4, 2006
Appl. No.: 10/191,880
Filed: Jul. 9, 2002

Related U.S. Application Data

(60) Provisional application No. 60/304,019, filed on Jul. 9, 2001.

(51) Int. Cl.
*A61K 33/04* (2006.01)

(52) U.S. Cl. .............................. 424/401; 424/59; 424/60; 424/400; 424/703; 514/859; 514/861; 514/863; 514/864

(58) Field of Classification Search ........................ None
See application file for complete search history.

(56) References Cited

U.S. PATENT DOCUMENTS 4,847,071 A * 7/1989 Bissett et al.
5,567,420 A * 10/1996 McEleney et al.
6,514,489 B1 * 2/2003 Shacknai et al.
7,022,332 B2 * 4/2006 Stiefel

FOREIGN PATENT DOCUMENTS

CA 2161737 * 5/1997
EP 0692254 * 10/1993
WO 03006005 * 1/2003

OTHER PUBLICATIONS

Zoe Kececioglu Draelos, M.D., "Sunscreens", *Cosmetics in Dermatology*, Churchill Livingston Inc. (1990), pp. 164–166.*

*Suncreen Drug Products for Over–the Counter Human Use; Amendment to the Tentative Final Monograph, Enforcement Policy*, 63 Fed. Reg. 56584 (Oct. 22, 1998).*

*Effective Sunscreen Ingredients and Cutaneous Irritation in Patients With Rosacea*, Nichols et al, Cutis., vol. 61, No. 6, 1998, pp. 344–346.*

*The United States Pharmacopeia, Twentieth Revision*, Official from Jul. 1, 1980, United States Pharmacopeial Convention, Inc., p. 744.*

Physicians' Desk Reference, Sulfacet R® lotion Edition 31, (1977), pp. 755–756.*

*The treatment of rosacea: the safety and efficacy of sodium sulfacetamide 10% and sulfur 5% lotion (Novacet) is demonstrated in a double–blind study*, Sauder et al, J. Derm. Treat., (1997) 8, pp 79–85.*

Zoe Diana Draelos, MD, PA; "Cosmetics," http://www.emedicine.com/derm/topic502.htm, printed Aug. 8, 2006.

Cosmetic Ingredient Dictionary, "Search Results For: Silica," http://www.cosmeticcop.com/learn/dictionary.asp?keys=silica&pos=1&type=FIND, printed Aug. 8, 2006.

21 C.F.R. §352.10 (Apr. 1, 2006 edition), "Subpart B–Active Ingredients," http://www.access.gpo.gov/nara/cfr/waisidx_06/21cfr352_06.html, printed Aug. 8, 2006.

21 C.F.R. §352.76 (Apr. 1, 2006), "Determination if a product is water resistant or etc.," http://www.access.gpo.gov/nara/cfr/waisidx_06/21cfr352_06.html, printed Aug. 8, 2006.

Bradley Pharmaceuticals, Inc., "Sulfacet R labeling," http://www.bradphram.com/intl/dermik.html, printed Aug. 10, 2006.

Bradley Pharmaceuticals, Inc., "Sulfacet R labeling," http://www.bradpharm.com/intl/pdf/SULF2_lns.pdf, printed Aug. 10, 2006.

Mark G. Lebwohl, The Comparative Efficacy of Sodium Sulfacetamide . . . J. Geriatric Derm. 1995;3:191–195.

Stanislaw Bucchner, MD., "Rosacea: An Update," Dertmatology 2005;210:100–108.

Michelle T. Pelle, MD., Glen H. Crawford, MD., & William D. James, MD., "Continuing Medical Education: Rosacea: II. Therapy," J Am Acad Dermatol 2004:vol. 51, No. 4, 500–512.

Wells, F.V. & Lubowe, Irwin I. Cosmetics and the Skin. New York: Reinhold Publishing Corporation, 1964.

Rieger, Martin M., Ph.D. (Ed.). Harry's Cosmeticology (8th Ed). New York, NY: Chemical Publishing Co., 2000.

Phenonip(R), product brochure; Clariant UK Ltd.

* cited by examiner

*Primary Examiner*—Evelyn Huang

(57) ABSTRACT

The present invention provides improved sulfacetamide and sulfur formulations including sunscreens for the treatment of rosacea.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–60 are cancelled.

* * * * *